US012776570B2

(12) United States Patent
Sanchez Ortiz et al.

(10) Patent No.: US 12,776,570 B2
(45) Date of Patent: Oct. 27, 2026

(54) ANTENNA ASSEMBLY

(71) Applicant: KYOCERA AVX Components (San Diego), Inc., San Diego, CA (US)

(72) Inventors: Francisco Carlos Sanchez Ortiz, San Diego, CA (US); Weichun Eric Lin, San Diego, CA (US)

(73) Assignee: KYOCERA AVX Components (San Diego), Inc., San Diego, CA (US)

( * ) Notice: Subject to any disclaimer, the term of this patent is extended or adjusted under 35 U.S.C. 154(b) by 86 days.

(21) Appl. No.: 18/735,756

(22) Filed: Jun. 6, 2024

(65) Prior Publication Data

US 2024/0413524 A1 Dec. 12, 2024

Related U.S. Application Data

(60) Provisional application No. 63/506,488, filed on Jun. 6, 2023.

(51) Int. Cl.

| | |
|---|---|
| ***H01Q 1/27*** | (2006.01) |
| ***H01Q 1/24*** | (2006.01) |
| ***H01Q 23/00*** | (2006.01) |
| *A61C 8/00* | (2006.01) |
| *A61N 1/372* | (2006.01) |

(52) U.S. Cl.

CPC ............. *H01Q 1/273* (2013.01); *H01Q 23/00* (2013.01); *A61C 8/0093* (2013.01); *A61N 1/37229* (2013.01)

(58) Field of Classification Search

CPC ........... H01Q 1/273; H01Q 9/42; H01Q 23/00

See application file for complete search history.

(56) References Cited

U.S. PATENT DOCUMENTS

| | | | |
|---|---|---|---|
| 2018/0090843 | A1 | 3/2018 | Anderson |
| 2023/0030704 | A1 | 2/2023 | Weinstein et al. |
| 2023/0078536 | A1 | 3/2023 | Ergun et al. |

FOREIGN PATENT DOCUMENTS

| | | | | |
|---|---|---|---|---|
| CN | 207765606 U | * | 8/2018 | ............... H01Q 1/36 |
| CN | 209592304 U | | 11/2019 | |

OTHER PUBLICATIONS

PCT App. No. PCT/US2024/032520, International Search Report and Written Opinion, mailed Sep. 20, 2024, 19 pages.

* cited by examiner

*Primary Examiner* — Hoang V Nguyen

(74) *Attorney, Agent, or Firm* — Dority & Manning, P.A.

(57) ABSTRACT

An antenna assembly is provided. The antenna assembly includes a circuit board having a communication circuit. The antenna assembly further includes an antenna at least partially surrounding the circuit board. The antenna assembly further includes a conductive epoxy coupled to the antenna to establish an electrical connection between the communication circuit and the antenna.

19 Claims, 8 Drawing Sheets

ANTENNA ASSEMBLY

PRIORITY CLAIM

The present application is based on and claims priority to U.S. Provisional Application 63/506,488 having a filing date of Jun. 6, 2023, which is incorporated by reference herein.

FIELD

The present disclosure relates generally to an antenna assembly.

BACKGROUND

Antennas can be used to facilitate wireless communication between devices. It can be desirable for antennas to operate with a high antenna radiation efficiency to improve wireless communication between devices. Antennas may need to be incorporated into a variety of different types of devices to provide for wireless communication. With the advance of medical device technology, antennas are being incorporated into a variety of different medical devices, such as implanted devices, such as small, implanted devices.

SUMMARY

Aspects and advantages of embodiments of the present disclosure will be set forth in part in the following description, or may be learned from the description, or may be learned through practice of the embodiments.

One example embodiment of the present disclosure is directed to an antenna assembly. The antenna assembly includes a circuit board having a communication circuit. The antenna assembly further includes an antenna at least partially surrounding the circuit board. The antenna assembly further includes a conductive epoxy coupled to the antenna to establish an electrical connection between the communication circuit and the antenna.

Another example embodiment of the present disclosure is directed to a medical device. The medical device includes a housing. The medical device further includes an antenna assembly disposed in the housing. The antenna assembly includes a circuit board having a communication circuit. The antenna assembly further includes an antenna at least partially surrounding the circuit board. The antenna assembly further includes a conductive epoxy coupled to the antenna to establish an electrical connection between the communication circuit and the antenna.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

Detailed discussion of embodiments directed to one of ordinary skill in the art are set forth in the specification, which refers to the appended figures, in which.

DETAILED DESCRIPTION

Figure 1:
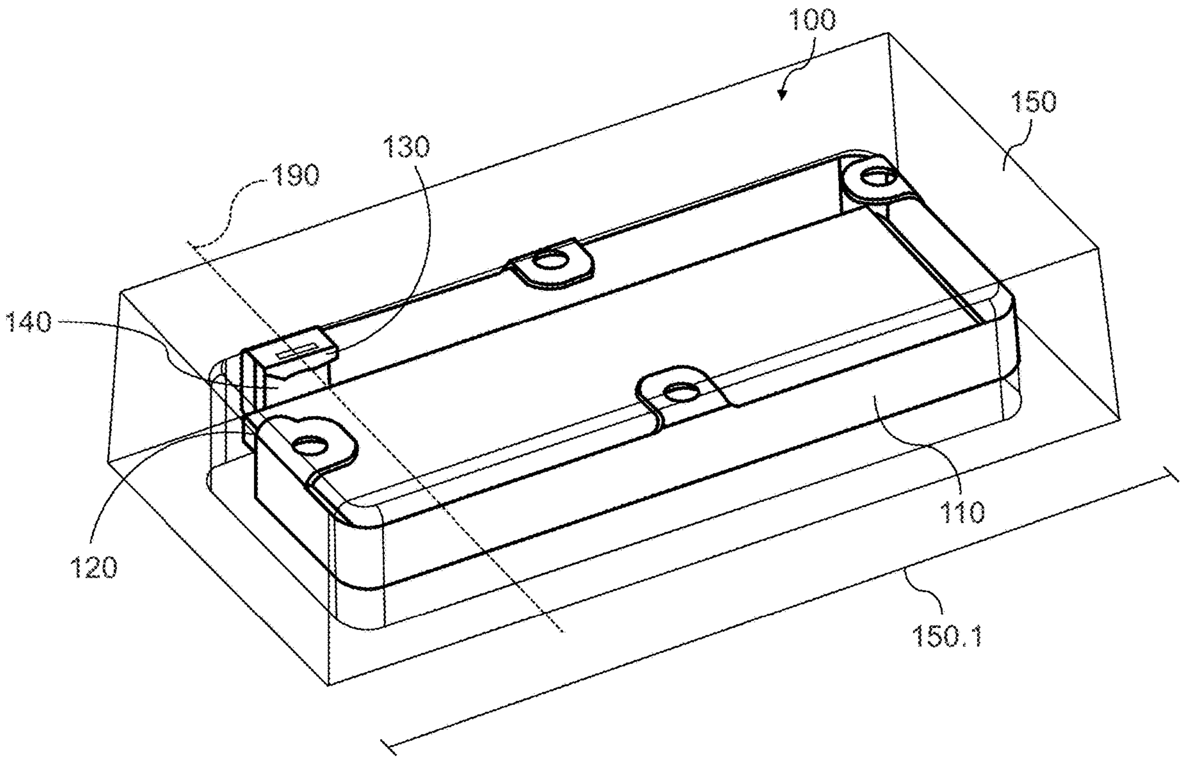
FIG. 1 depicts a top perspective view of an antenna assembly including a laser direct structuring (LDS) antenna according to example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations. As used herein, the use of the term "about" in conjunction with a numerical value is intended to refer to within 10% of the numerical value.

Example aspects of the present disclosure are directed to an antenna assembly for use in, for instance, a medical device, such as an implanted medical device, such as a dental implant. Integrating antennas into devices that are worn or placed near a human body can pose challenges due to degradation of RF signals by the human body. Due to the small nature of medical devices, connecting an antenna to communication circuitry on a printed circuit board may pose challenges. For instance, due to the small nature of certain medical devices (e.g., devices having a longest dimension of less than about 20 mm), using solder to connect an antenna to a printed circuit board may be difficult as the solder may be exposed to other components of the device, leading to anomalies and malfunctioning of the device.

According to example embodiments of the present disclosure, an antenna assembly may include an antenna. The antenna may be a laser direct structuring (LDS) antenna, a stamped metal antenna, or other suitable antenna. The antenna may have a shape such that the antenna is disposed around a peripheral portion of the device. The antenna may be disposed at least partially around a printed circuit board, such as around at least 90% of the printed circuit board, such as at least 80% of the printed circuit board, such as at least 75% of the printed circuit board. The printed circuit board may include a communication circuit (e.g., transmission line, transceiver, receiver, transmitter, front end module, matching circuit, etc.) to facilitate communication of information over the antenna. At least a portion of the antenna may be co-planar with the printed circuit board.

In some embodiments, the antenna may be coupled to the communication circuitry using a metal contact. In some embodiments, the metal contact may be an L-shaped metal contact. The L-shaped metal contact may have a first leg and a second leg. In some embodiments, the first leg may have a longer length dimension (e.g., long dimension) relative to the second leg. Alternatively, the first leg may have a shorter length dimension relative to the second leg, or a length dimension that is the same as the length dimension of the second leg. The second leg of the L-shaped metal contact may be coupled to or on the printed circuit board. The first leg of the L-shaped metal contact may extend to the antenna.

The antenna may be coupled to the metal contact using a conductive epoxy. In some examples, the housing of the device (e.g., medical device) may include a cavity or recess. The cavity or recess may accommodate the conductive epoxy to couple the antenna to the metal contact. The conductive epoxy may be, for instance, an electrically conductive epoxy adhesive. The conductive epoxy may include, for instance, conductive fillers (e.g., particles, flakes) in an epoxy matrix. The conductive fillers may be, for instance, silver or other metal or electrically conductive material.

The conductive epoxy may couple the L-shaped metal contact to the antenna to establish an electrical connection between the communication circuit and the antenna. The electrical connection, in some embodiments, may be a solder free connection.

In some embodiments, the antenna may be coupled extend at least partially through the circuit board. For instance, the antenna may extend at least partially into a recess (e.g., a through hole) defined in the printed circuit board. The recess (e.g., through hole) may include a conductive epoxy to establish an electrical connection between the antenna and a communication circuit on the circuit board.

FIGS. 1-4 depict various views of an antenna assembly according to example embodiments of the present disclosure. The antenna assembly may be in a housing (e.g., a housing associated with a medical device). The antenna assembly includes an antenna that may be an LDS antenna. The antenna (e.g., LDS antenna) may partially surround a printed circuit board (PCB). The PCB has a communication circuit. A metal contact, such as an L-shaped metal contact, may couple the PCB (e.g., communication circuit) to the antenna using a conductive epoxy. The conductive epoxy may establish an electrical connection between the antenna and the communication circuit (e.g., through the metal contact). The conductive epoxy may be disposed in a recess or cavity of the housing.

Referring now to FIG. 1 specifically, a top perspective view of antenna assembly 100 is illustrated. Antenna assembly 100 may be disposed in a housing 150 (e.g., in a cavity defined in housing 150). In some embodiments, housing 150 may be associated with a medical device. For example, housing 150 may be implemented within a medical device such as, for example, an implanted medical device. For example, housing 150 may be associated with a dental implant. In some embodiments, housing 150, along with antenna assembly 100, may be a medical device, such as an implanted medical device, such as a dental implant. As such, FIGS. 1-4 may depict a medical device according to example embodiments of the present disclosure, In some embodiments, housing 150 has a length 150.1 (e.g., long dimension) of less than about 20 mm. As shown in FIG. 1, antenna assembly 100 may include a circuit board 120, such as a printed circuit board (PCB). Circuit board 120 may include a communication circuit (e.g., transmission line, transceiver, receiver, transmitter, front end module, matching circuit, etc.) to facilitate communication of information over antenna 110.

Antenna assembly 100 further includes an antenna 110. While antenna 110 is depicted in FIG. 1 as an LDS antenna, those of ordinary skill in the art will understand that antenna 110 may be any suitable antenna. As shown, antenna 110 may partially surround circuit board 120. Antenna 110 may have a shape such that antenna 110 is disposed around a peripheral portion of the device. Antenna 110 may be disposed at least partially around circuit board 120 (e.g., printed circuit board), such as around at least 90% of the circuit board 120, such as at least 80% of the circuit board 120, such as at least 75% of the circuit board 120. At least a portion of antenna 110 may be co-planar with the circuit board 120.

Antenna assembly 100 may further include a conductive epoxy 130. Conductive epoxy 130 may be coupled to antenna 110 to establish an electrical connection between circuit board 120 (e.g., communication circuit of circuit board 120) and antenna 110. The conductive epoxy 130 may be, for instance, an electrically conductive epoxy adhesive. The conductive epoxy 130 may include, for instance, conductive fillers (e.g., particles, flakes) in an epoxy matrix. The conductive fillers may be, for instance, silver or other metal or electrically conductive material. In some embodiments, antenna 110 may be coupled to the communication circuitry of the circuit board 120 using a contact 140 (e.g., metal contact, L-shaped metal contact).

Figure 2:
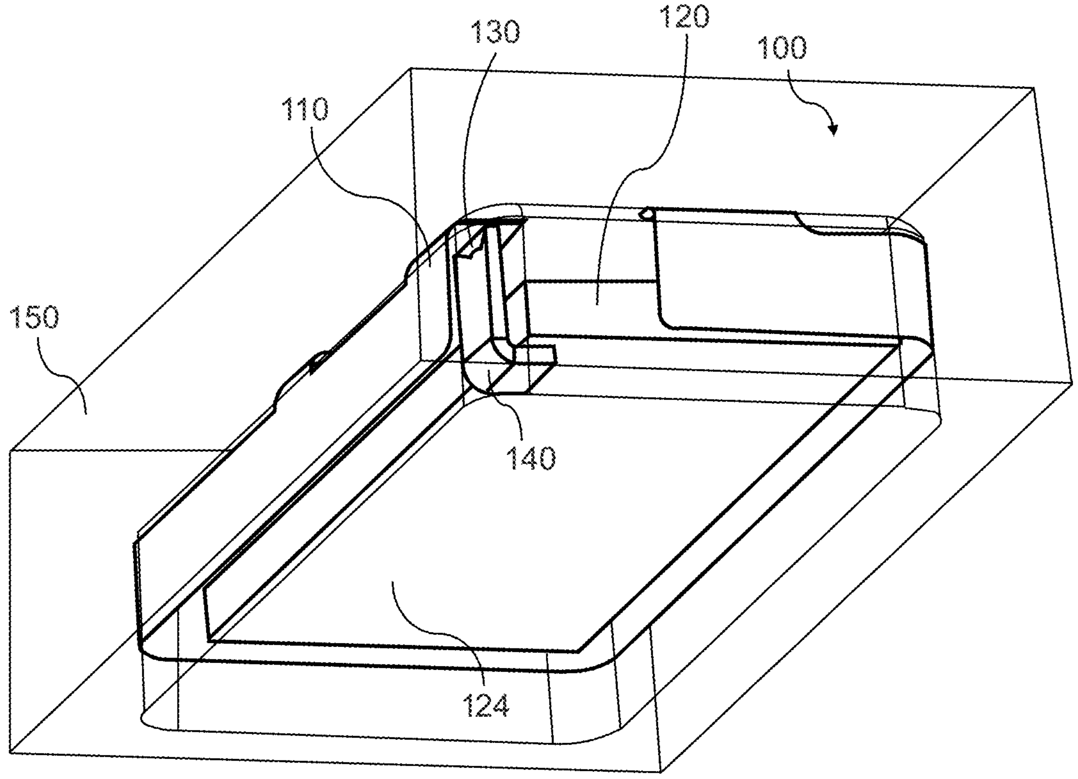
FIG. 2 depicts a bottom perspective view of an antenna assembly including an LDS antenna according to example embodiments of the present disclosure.

As shown in FIG. 2, contact 140 (e.g., metal contact) may be an L-shaped contact (e.g., L-shaped metal contact) extending between circuit board 120 and antenna 110. Specifically, contact 140 may extend from a bottom surface 124 of circuit board 120 to antenna 110. In some embodiments, conductive epoxy 130 may be coupled to contact 140. For example, conductive epoxy may be used to couple contact 140 to antenna 110.

Figure 3:
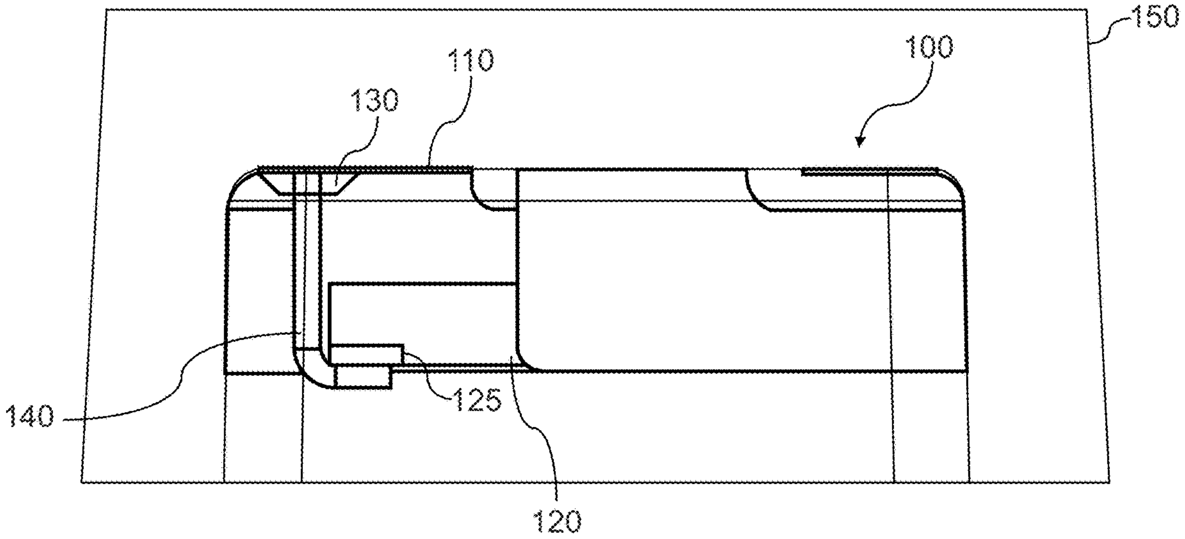
FIG. 3 depicts side view of an antenna assembly including an LDS antenna according to example embodiments of the present disclosure.

Referring now to FIG. 3, a side view of antenna assembly 100 is illustrated. As shown in FIG. 3, conductive epoxy 130 may establish an electrical connection between the antenna 110 and the communication circuit 125 of circuit board 120 (e.g., through contact 140). In some embodiments, conductive epoxy 130 may be disposed in a recess or cavity of the housing 150.

Figure 4:
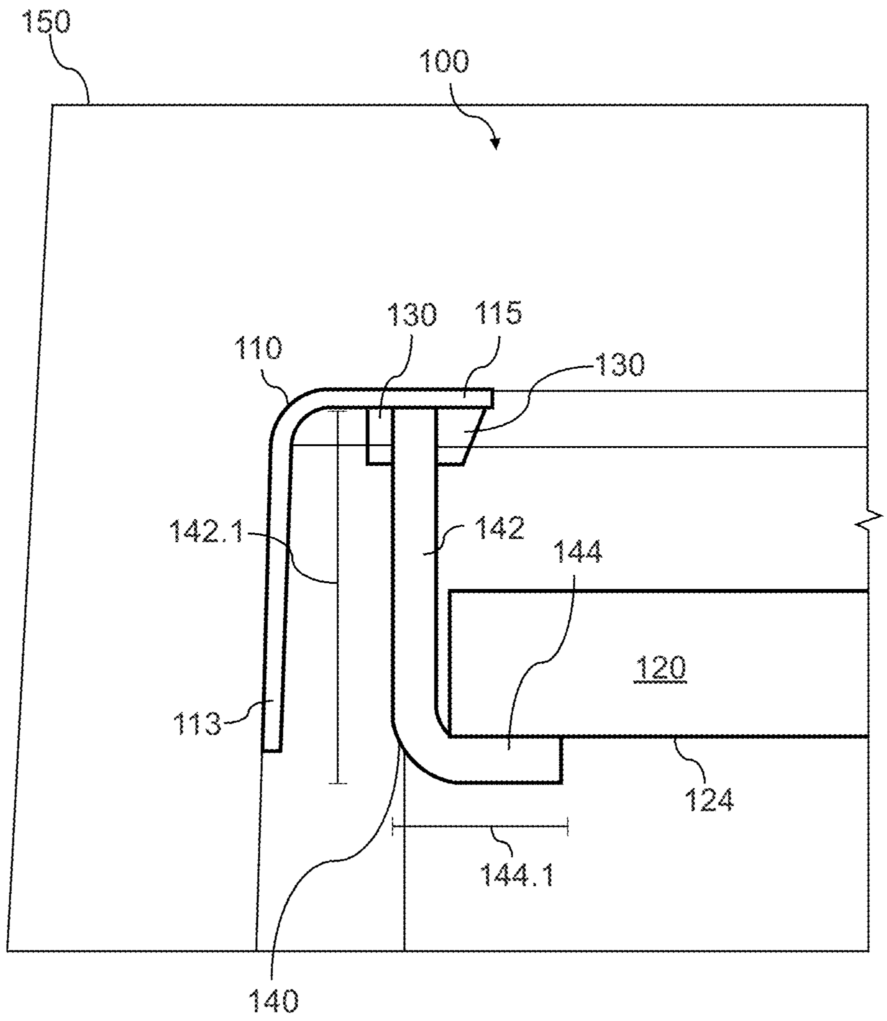
FIG. 4 depicts a cross-sectional view of the antenna assembly of FIG. 1.

FIG. 4 depicts a blown-up cross-sectional view of the antenna assembly 100 taken along line 190 (FIG. 1). As shown in FIG. 4, contact 140 may include a first leg 142 and a second leg 144. First leg 142 may be electrically coupled to antenna 110 via conductive epoxy 130. Second leg 144 may be coupled to or on circuit board 120. In some embodiments, first leg 142 may have a longer length dimension 142.1 (e.g., long dimension) relative to the length dimension 144.1 of the second leg 144. In alternative embodiments, length dimension 142.1 of first leg 142 may be shorter than (e.g., less than) length dimension 144.1 of the second leg 144. In other alternative embodiments, length dimension 142.1 of first leg 142 may be about the same length as length dimension 144.1 of the second leg 144.

As previously described, a portion of antenna 110 may be co-planar with the printed circuit board 120. In some embodiments, antenna 110 may be defined as including a first portion 113 and a second portion 115. As shown in FIG. 4, second portion 115 of antenna 110 may be co-planar with circuit board 120 and second leg 144 of contact 140 (e.g., along length dimension 144.1). Similarly, first portion 113 of antenna 110 may be co-planar with first leg 142 of contact

140 (e.g., along length dimension 142.1). Contact 140 (e.g., first leg 142 of contact 140) may be coupled to a bottom surface of the second portion 115 of antenna 110 with, for example, conductive epoxy 130.

FIGS. 5-8 depict various views of an antenna assembly according to example embodiments of the present disclosure. The antenna assembly may be in a housing (e.g., a housing associated with a medical device). The antenna assembly includes an antenna, such as a stamped metal antenna. The antenna (e.g., stamped metal antenna) may at least partially surround a printed circuit board (PCB). The PCB may have a recess (e.g., through hole). At least a portion of the antenna may extend at least partially into the PCB (e.g., all the way through the PCB). A conductive epoxy may establish an electrical connection between the antenna and the communication circuit. The conductive epoxy may be disposed in the recess (e.g., through hole) of the PCB.

Figure 5:
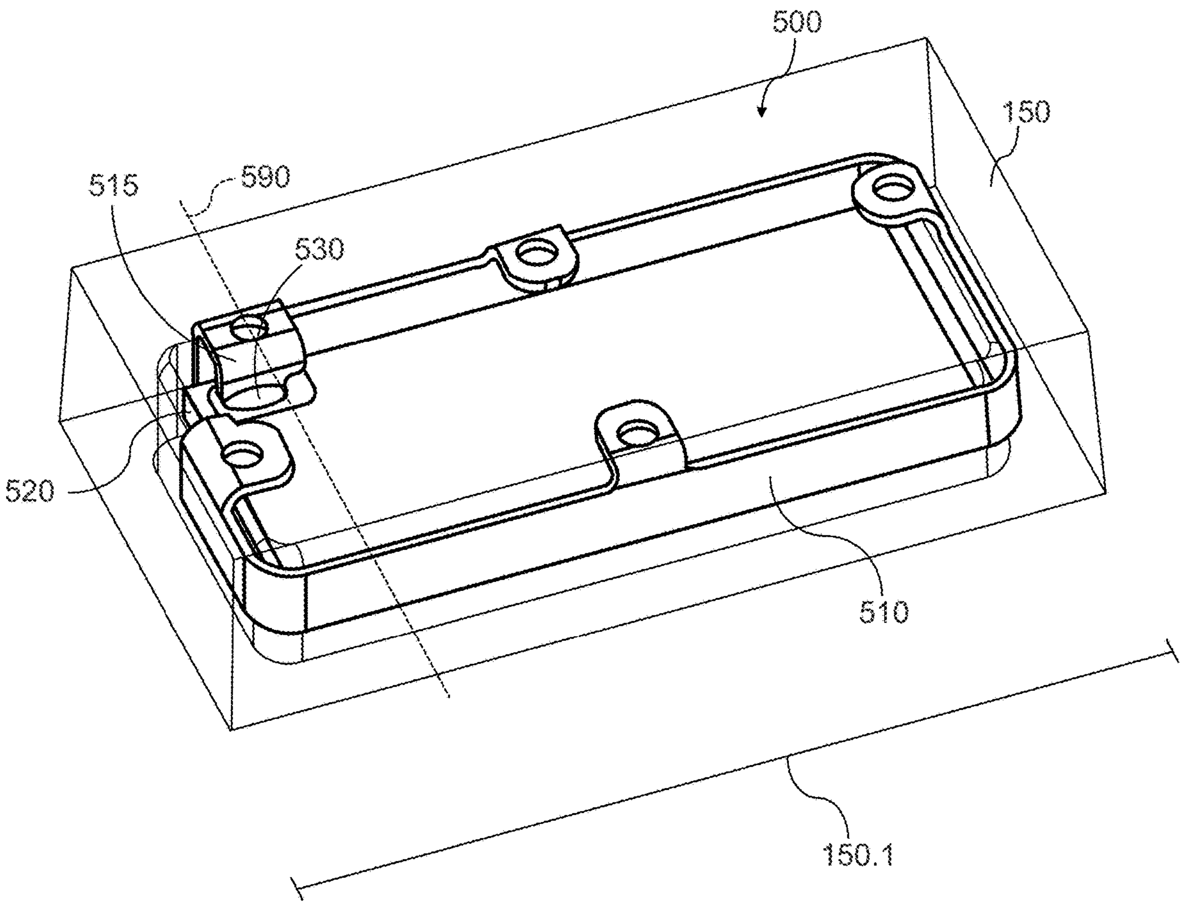
FIG. 5 depicts a top perspective view of an antenna assembly including a stamped metal antenna according to example embodiments of the present disclosure.

Referring now to FIG. 5, a top perspective view of antenna assembly 500 is illustrated. Antenna assembly 500 may be disposed in a housing 150 (e.g., a housing associated with a medical device, a housing associated with a dental implant). In some embodiments, housing 150 has a length 150.1 (e.g., long dimension) of less than about 20 mm.

As shown in FIG. 5, antenna assembly 500 may include a circuit board 520, such as a printed circuit board (PCB). Circuit board 520 may include a communication circuit (e.g., transmission line, transceiver, receiver, transmitter, front end module, matching circuit, etc.) to facilitate communication of information over antenna 510.

Antenna assembly 500 further includes an antenna 510. While antenna 510 is depicted in FIG. 5 as a stamped metal antenna, those of ordinary skill in the art will understand that antenna 510 may be any suitable antenna. The antenna 510 partially surrounds circuit board 520. Antenna 510 may have a shape such that antenna 510 is disposed around a peripheral portion of the device. Antenna 510 may be disposed at least partially around circuit board 520 (e.g., printed circuit board), such as around at least 90% of the circuit board 520, such as at least 80% of the circuit board 520, such as at least 75% of the circuit board 520. At least a portion of antenna 510 may be co-planar with the circuit board 520.

Antenna assembly 500 further includes a conductive epoxy 530. Conductive epoxy 530 may be coupled to antenna 510 to establish an electrical connection between circuit board 520 (e.g., communication circuit of circuit board 520) and antenna 510. The conductive epoxy 530 may be, for instance, an electrically conductive epoxy adhesive. The conductive epoxy 530 may include, for instance, conductive fillers (e.g., particles, flakes) in an epoxy matrix. The conductive fillers may be, for instance, silver or other metal or electrically conductive material.

Figure 6:
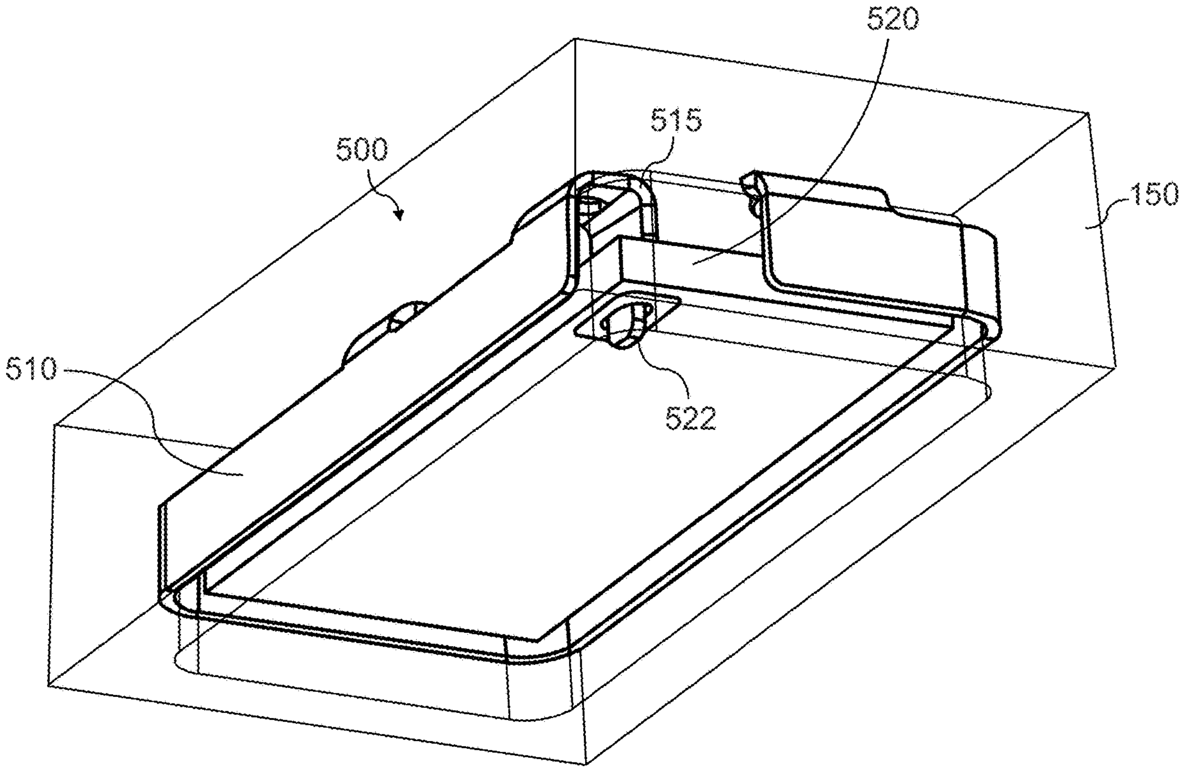
FIG. 6 depicts a bottom perspective view of an antenna assembly including a stamped metal antenna according to example embodiments of the present disclosure.

In some embodiments, housing 150, along with antenna assembly 500, may be a medical device, such as an implanted medical device, such as a dental implant. As such, FIGS. 5-8 may depict a medical device according to example embodiments of the present disclosure, Referring now to FIG. 6, a bottom perspective view of antenna assembly 500 is illustrated. As shown in FIG. 6, circuit board 520 may include recess 522. Recess 522 may be a through hole extending entirely through circuit board 520. As such, a portion 515 of antenna 510 may extend at least partially through circuit board 520 in recess 522 defined in circuit board 520. In some embodiments, portion 515 of antenna 510 may extend completely through recess 522 defined in circuit board 520.

Figure 7:
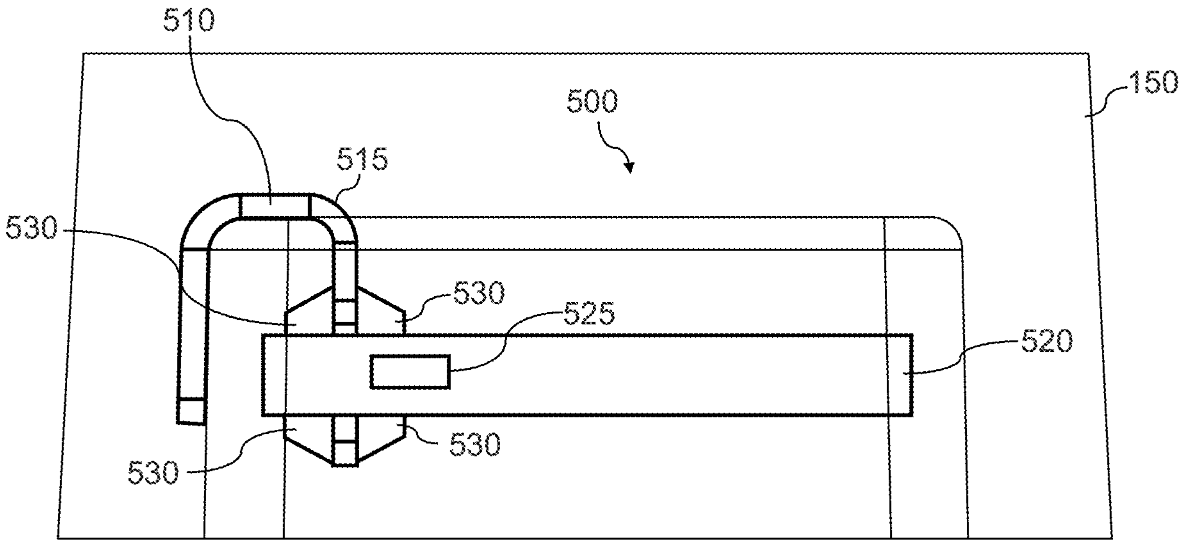
FIG. 7 depicts side view of an antenna assembly including a stamped metal antenna according to example embodiments of the present disclosure.

Referring now to FIG. 7, a side view of antenna assembly 500 is illustrated. As shown in FIG. 7, circuit board 520 of antenna assembly 500 may include a communication circuit 525 (e.g., transmission line, transceiver, receiver, transmitter, front end module, matching circuit, etc.) to, for example, facilitate communication of information over antenna 510. Conductive epoxy 530 may establish an electrical connection between the antenna 510 (e.g., portion 515 of antenna 510) and the communication circuit 525 of circuit board 520. In some embodiments, conductive epoxy 530 may be disposed in a recess or cavity of the housing 150 to connect antenna 510 to communication circuit 525. For example, antenna 510 (e.g., portion 515 of antenna 510) may not physically contact circuit board 520. As such, conductive epoxy 530 may be configured to electrically connect antenna 510 (e.g., portion 515 of antenna 510) to circuit board 520 (e.g., communication circuit 525 of circuit board 520).

Figure 8:
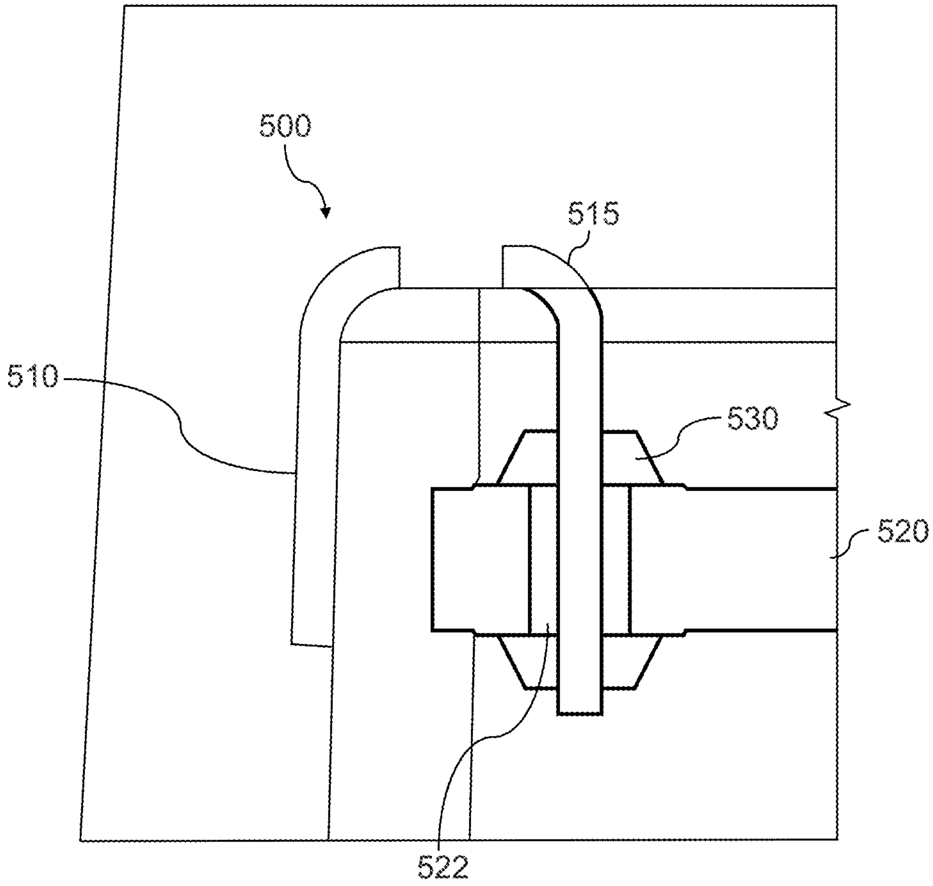
FIG. 8 depicts a cross-sectional view of the antenna assembly of FIG. 5.

FIG. 8 depicts a blown-up cross-sectional view of the antenna assembly 500 taken along line 590 (FIG. 5). As shown in FIG. 8, antenna 510 (e.g., portion 515 of antenna 510) may extend (e.g., at least partially extend, extend entirely) through circuit board 520 in recess 522 defined in circuit board 520. Conductive epoxy 530 is disposed (e.g., at least partially disposed) in recess 522 such that antenna 510 may be electrically connected to circuit board 520. In some embodiments, antenna 510 (e.g., portion 515 of antenna 510) may not physically contact circuit board 520. As such, conductive epoxy 530 may be configured to electrically connect antenna 510 (e.g., portion 515 of antenna 510) to circuit board 520.

One example embodiment of the present disclosure is directed to an antenna assembly. The antenna assembly includes a circuit board having a communication circuit. The antenna assembly further includes an antenna at least partially surrounding the circuit board. The antenna assembly further includes a conductive epoxy coupled to the antenna to establish an electrical connection between the communication circuit and the antenna.

In some examples, the antenna is an LDS antenna.

In some examples, the antenna assembly further includes an L-shaped metal contact extending between the circuit board and the antenna, wherein the conductive epoxy is coupled to the L-shaped metal contact.

In some examples, the L-shaped metal contact comprises a first leg and a second leg, the first leg having a longer length than the second leg.

In some examples, the second leg is on the circuit board.

In some examples, the first leg extends to the antenna.

In some examples, the antenna is a stamped metal antenna.

In some examples, at least a portion of the antenna extends at least partially through the circuit board in a recess defined in the circuit board.

In some examples, the conductive epoxy is disposed at least partially in the recess.

In some examples, the recess is a through hole extending entirely through the circuit board.

In some examples, the antenna assembly is disposed in a housing.

In some examples, the housing is associated with a medical device.

In some examples, the housing is associated with a dental implant.

In some examples, the housing has a long dimension of less than about 20 mm.

Another example embodiment of the present disclosure is directed to a medical device. The medical device includes a housing. The medical device further includes an antenna assembly disposed in the housing. The antenna assembly includes a circuit board having a communication circuit. The antenna assembly further includes an antenna at least partially surrounding the circuit board. The antenna assembly further includes a conductive epoxy coupled to the antenna to establish an electrical connection between the communication circuit and the antenna.

In some examples, the medical device is an implanted medical device.

In some examples, the medical device is a dental implant.

In some examples, the housing has a long dimension of less than about 20 mm.

In some examples, the antenna is an LDS antenna.

In some examples, the antenna is a stamped metal antenna.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An antenna assembly, comprising:
a circuit board having a communication circuit;
an antenna extending along one or more planes, each plane parallel to a side of the circuit board, the antenna including a first portion and a second portion; and
an L-shaped metal contact extending between the circuit board and the antenna, the L-shaped metal contact configured to establish an electrical connection between the communication circuit and the antenna, the L-shaped metal contact comprising a first leg and a second leg, wherein the first portion of the antenna is co-planar with the first leg, and the second portion of the antenna is co-planar with the circuit board and the second leg.

2. The antenna assembly of claim 1, wherein the first leg having a longer length than the second leg.

3. The antenna assembly of claim 2, wherein the second leg is coupled to the circuit board.

4. The antenna assembly of claim 3, wherein the first leg extends to the antenna.

5. The antenna assembly of claim 4, wherein
the first portion of the antenna extends along a first plane parallel to a first side of the circuit board,
wherein the first side of the circuit board is greater in length than a second side of the circuit board, the second side adjacent to the first side.

6. The antenna assembly of claim 1, wherein the antenna assembly is disposed in a housing.

7. The antenna assembly of claim 6, wherein the housing has a long dimension of less than about 20 mm.

8. The antenna assembly of claim 6, wherein the housing is associated with a medical device.

9. The antenna assembly of claim 6, wherein the housing is associated with a dental implant.

10. The antenna assembly of claim 1, wherein at least a portion of the antenna extends at least partially through the circuit board in a recess defined in the circuit board.

11. The antenna assembly of claim 1, wherein the antenna is an LDS antenna.

12. The antenna assembly of claim 1, wherein the antenna is a stamped metal antenna.

13. A medical device, comprising:
a housing; and
an antenna assembly disposed in the housing, the antenna assembly comprising:
a circuit board having a communication circuit;
an antenna extending along one or more planes, each plane parallel to a side of the circuit board, the antenna including a first portion and a second portion; and
an L-shaped metal contact extending between the circuit board and the antenna, the L-shaped metal contact configured to establish an electrical connection between the communication circuit and the antenna, the L-shaped metal contact comprising a first leg and a second leg, wherein the first portion of the antenna is co-planar with the first leg, and the second portion of the antenna is co-planar with the circuit board and the second leg.

14. The medical device of claim 13, wherein the first leg of the antenna having a longer length than the second leg.

15. The medical device of claim 13, wherein the housing has a long dimension of less than about 20 mm.

16. The medical device of claim 13, wherein at least a portion of the antenna extends at least partially through the circuit board in a recess defined in the circuit board.

17. The medical device of claim 13, wherein the antenna is an LDS antenna.

18. The medical device of claim 13, wherein the antenna is a stamped metal antenna.

19. The medical device of claim 13, wherein the housing is associated with a dental implant.

* * * * *